US00PP24908P2

(12) United States Plant Patent
Misato

(10) Patent No.: US PP24,908 P2
(45) Date of Patent: Sep. 23, 2014

(54) *MANDEVILLA* PLANT NAMED 'SUNPARASURE'

(50) Latin Name: *Mandevilla hybrida*
Varietal Denomination: Sunparasure

(75) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 173 days.

(21) Appl. No.: 13/506,174

(22) Filed: Mar. 31, 2012

(51) Int. Cl.
*A01H 5/00* (2006.01)

(52) U.S. Cl.
USPC ..... Plt./232

(58) Field of Classification Search
CPC ..... A01H 5/02
USPC ..... Plt./232
See application file for complete search history.

(56) References Cited

PUBLICATIONS

Pluto Upov Plant Variety Database 201303, retrieved on Nov. 20, 2013, retrieved from the Internet at <https://www3.wipo.int/pluto/user/en/index.jsp> for *Mandevilla* 'Sunparavelre', 2 pp.*

* cited by examiner

*Primary Examiner* — June Hwu
(74) *Attorney, Agent, or Firm* — C. A. Whealy

(57) ABSTRACT

A new and distinct cultivar of *Mandevilla* plant named 'Sunparasure', characterized by its compact and vining plant habit; vigorous growth habit; freely branching habit and short internodes, dense and bushy plant form; freely flowering habit; long flowering period; and large bright red-colored flowers.

1 Drawing Sheet

Botanical designation: *Mandevilla hybrida.*
Cultivar denomination: 'SUNPARASURE'.

BACKGROUND OF THE INVENTION

The present invention relates to a new and distinct cultivar of *Mandevilla* plant, botanically known as *Mandevilla hybrida* and hereinafter referred to by the name 'Sunparasure'.

The new *Mandevilla* plant is a product of a planned breeding program conducted by the Inventor in Higashiomi, Shiga, Japan. The objective of the breeding program is to create new freely-branching and vining *Mandevilla* plants with numerous bright red-colored flowers.

The new *Mandevilla* plant originated from an open-pollination in Higashiomi, Shiga, Japan in April, 2006 of a proprietary selection of *Mandevilla hybrida* identified as code number M8997, not patented, as the female, or seed parent with an unknown selection of *Mandevilla hybrida*, as the male, or pollen, parent. The new *Mandevilla* plant was discovered and selected by the Inventor as a single flowering plant from within the progeny of the stated open-pollination in a controlled greenhouse environment in Higashiomi, Shiga, Japan in October, 2007.

Asexual reproduction of the new *Mandevilla* plant by cuttings in Higashiomi, Shiga, Japan since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparasure'. These characteristics in combination distinguish 'Sunparasure' as a new and distinct *Mandevilla* plant:

1. Compact and vining plant habit.
2. Vigorous growth habit.
3. Freely branching habit and short internodes, dense and bushy plant form.
4. Freely flowering habit.
5. Long flowering period.
6. Large bright red-colored flowers.

Plants of the new *Mandevilla* can be compared to plants of the female parent selection. Plants of the new *Mandevilla* differ primarily from plants of the female parent selection in flower color as plants of the female parent selection have rose pink-colored flowers. In addition, plants of the new *Mandevilla* had larger flowers than plants of the female parent selection.

Plants of the new *Mandevilla* can be compared to plants of the *Mandevilla* 'Sunparacore', disclosed in U.S. Plant Pat. No. 23,959. In side-by-side comparisons conducted in Higashiomi, Shiga, Japan, plants of the new *Mandevilla* differed from plants of 'Sunparacore' in the following characteristics:

1. Plants of the new *Mandevilla* had longer and thicker lateral branches than plants of 'Sunparacore'.
2. Plants of the new *Mandevilla* had shorter and broader leaves than plants of 'Sunparacore'.
3. Plants of the new *Mandevilla* and 'Sunparacore' differed in flower color as plants of 'Sunparacore' had dark red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparasure' grown in a container.

The photograph at the bottom of the sheet is a close-up view of a typical flower of 'Sunparasure'.

DETAILED BOTANICAL DESCRIPTION

The aforementioned photographs and following observations, measurements and values describe plants grown during the early autumn in 15-cm containers in an outdoor nursery in Higashiomi, Shiga, Japan and under commercial cultural practices. During the production of the plants, day temperatures averaged 25° C. and night temperatures averaged 15° C. Plants were five months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparasure'.

Parentage:

*Female, or seed, parent*.—Proprietary selection of *Mandevilla hybrida* identified as code number M8997, not patented.

*Male, or pollen, parent*.—Unknown selection of *Mandevilla hybrida*, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Compact and vining plant habit; vigorous growth habit; freely branching habit.

*Lateral branch description*.—Length: About 164.8 cm. Diameter: About 2.8 mm. Internode length: About 3.1 cm. Strength: Strong. Texture: Smooth, glabrous. Color, developing: Close to 144A. Color, mature: Close to 175A.

Foliage description:

*Arrangement*.—Opposite, simple.

*Length*.—About 6 cm.

*Width*.—About 4.3 cm.

*Shape*.—Elliptical.

*Apex*.—Cuspidate.

*Base*.—Obtuse.

*Margin*.—Entire.

*Texture, upper and lower surfaces*.—Smooth, glabrous.

*Venation pattern*.—Pinnate, reticulate.

*Color*.—Developing leaves, upper surface: Close to 146B. Developing leaves, lower surface: Close to 147C. Fully expanded leaves, upper surface: Close to N137C; venation, close to N144D. Fully expanded leaves, lower surface: Close to 138B; venation, close to 145D.

*Petiole length*.—About 1.7 cm.

*Petiole diameter*.—About 1.3 mm.

*Petiole texture, upper and lower surfaces*.—Smooth, glabrous.

*Petiole color, upper and lower surfaces*.—Close to 143B tinted with close to 175C.

Flower description:

*Flower type and habit*.—Single salverform flowers arranged in axillary racemes; flowers face upright to outwardly; freely flowering habit with about two to five flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—Present, pleasant.

*Inflorescence height*.—About 14 cm.

*Inflorescence diameter*.—About 12.5 cm.

*Flowers*.—Appearance: Flared trumpet, corolla fused and five-parted; flowers roughly star-shaped. Diameter: About 7.7 cm. Depth (length): About 6.4 cm. Throat diameter: About 1.8 cm. Tube length: About 5 cm. Tube diameter, mid-section: About 1.5 cm. Tube diameter, base: About 3.5 mm.

*Flower buds*.—Height: About 7.1 cm. Diameter: About 1.3 cm. Shape: Lenticular. Color: Close to 185A.

*Corolla*.—Quantity and arrangement: Five petals arranged in a single whorl and fused at the base. Petal length: About 3.7 cm. Petal width: About 3.3 cm. Petal shape: Orbicular. Petal apex: Cuspidate. Petal margin: Entire. Petal texture, upper and lower surfaces: Smooth, glabrous. Throat texture: Smooth, glabrous. Tube texture: Smooth, glabrous. Color: Petal, when opening and fully opened, upper surface: Close to 46B. Petal, when opening and fully opened, lower surface: Close to 53D. Throat: Towards the petal, close to 53A; towards the base, close to N25A. Tube: Close to 54D; towards the base, close to 2D.

*Calyx*.—Quantity and arrangement: Five sepals arranged in a single whorl. Sepal length: About 8.8 mm. Sepal width: About 2.3 mm. Sepal shape: Trullate. Sepal apex: Acuminate. Sepal base: Obtuse. Sepal margin: Entire. Sepal texture, upper and lower surfaces: Smooth, glabrous. Sepal color: When developing, upper and lower surfaces: Close to 144B; towards the apex, close to 64D. Fully developed, upper and lower surfaces: Close to 144B; towards the apex, close to 64D.

*Peduncles*.—Length: About 2.2 cm. Diameter: About 1.7 mm. Texture: Smooth, glabrous. Strength: Flexible, but strong. Color: Close to 143B.

*Pedicels*.—Length: About 1.9 cm. Diameter: About 2.3 mm. Texture: Smooth, glabrous. Strength: Flexible, but strong. Color: Close to 174A.

*Reproductive organs*.—Stamens: Quantity and arrangement: Typically five; filaments fused to corolla; anthers, connivent. Anther shape: Ellipsoidal. Anther size: About 0.9 mm by 10.3 mm. Anther color: Close to 12C. Pollen amount: Moderate. Pollen color: Close to 12C. Pistils: Quantity: Typically one. Pistil length: About 2.2 cm. Style color: Close to 4D. Stigma shape: Conical. Stigma color: Close to 4C. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparasure' as illustrated and described.

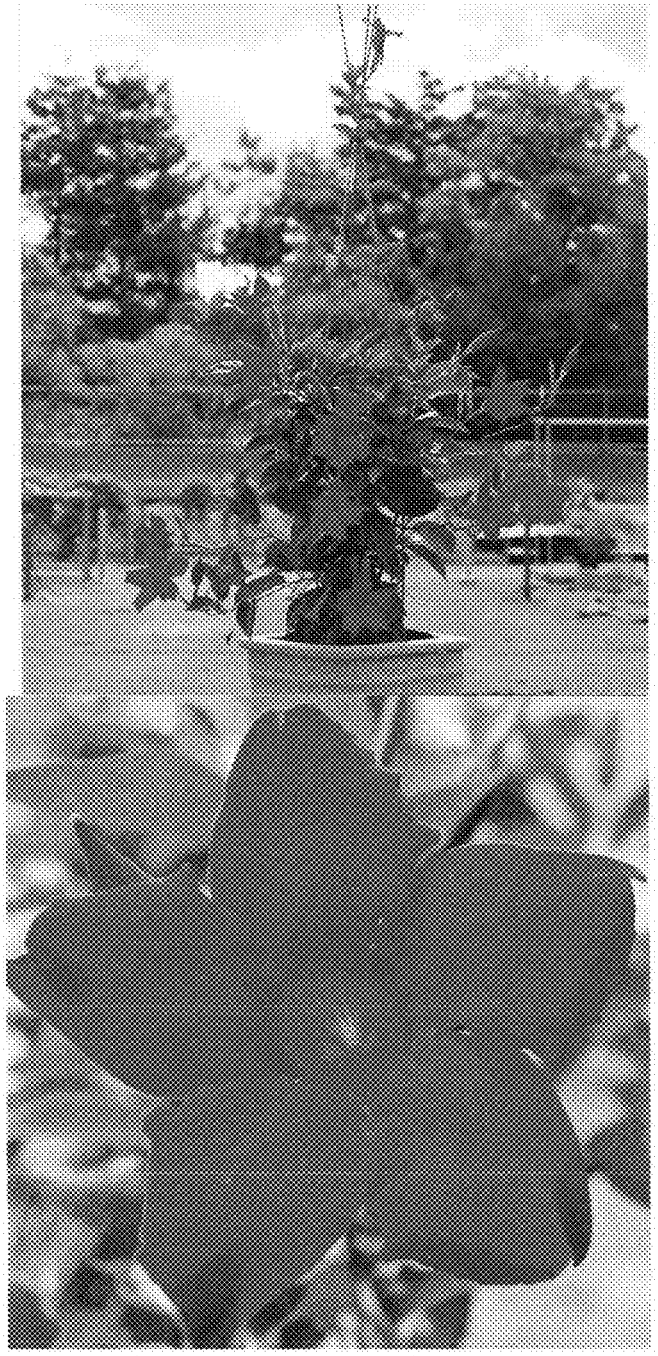

* * * * *